United States Patent [19]

Lapcevic

[11] Patent Number: 4,681,545
[45] Date of Patent: Jul. 21, 1987

[54] METHOD FOR RAPID OBTURATION OF ROOT CANALS

[76] Inventor: Robert E. Lapcevic, 12451 Curry Ct., Saratoga, Calif. 95070

[21] Appl. No.: 880,931

[22] Filed: Jun. 23, 1986

Related U.S. Application Data

[63] Continuation of Ser. No. 511,373, Jul. 5, 1983, abandoned.

[51] Int. Cl.⁴ .............................................. A61C 5/02
[52] U.S. Cl. ..................................... 433/224; 433/27; 433/228.1
[58] Field of Search ................. 433/224, 173, 27, 228

[56] References Cited

U.S. PATENT DOCUMENTS

| | | | |
|---|---|---|---|
| 1,463,963 | 8/1923 | Miller | 433/224 |
| 3,899,830 | 8/1975 | Malmin | 433/224 |
| 4,480,996 | 11/1984 | Crovatto | 433/164 |
| 4,525,147 | 6/1985 | Pitz et al. | 433/224 |

FOREIGN PATENT DOCUMENTS 2728494 1/1979 Fed. Rep. of Germany ...... 433/224

Primary Examiner—John J. Wilson
Attorney, Agent, or Firm—Townsend & Townsend

[57] ABSTRACT

A method and system for obturating root canals are disclosed. The system includes filling points which are formed from a thermoplastic material and include an internal heating element axially aligned therein. By inserting the filling point into a prepared root canal and applying a moderate downward pressure thereon with an instrument which is capable of heating the heating element in situ, the thermoplastic material can be softened to effectively seal the main root canal and accessory canals without the need to insert instruments down into the canal system.

15 Claims, 17 Drawing Figures

U.S. Patent   Jul. 21, 1987   Sheet 1 of 2   4,681,545
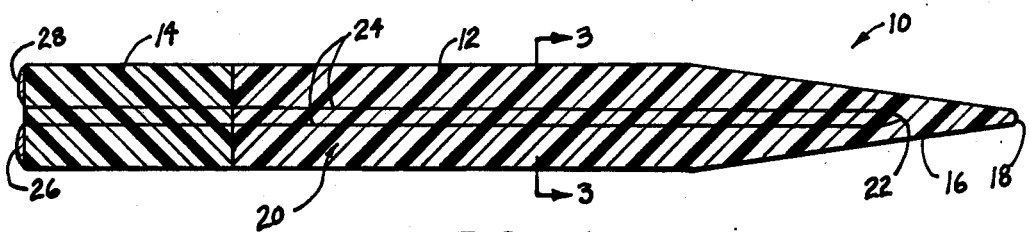
FIG._1.
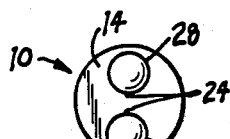
FIG._2.
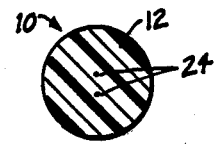
FIG._3.
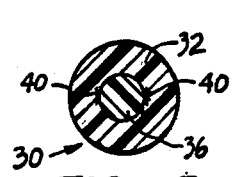
FIG._5.
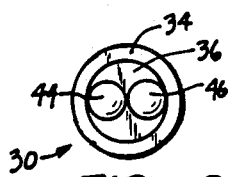
FIG._6.
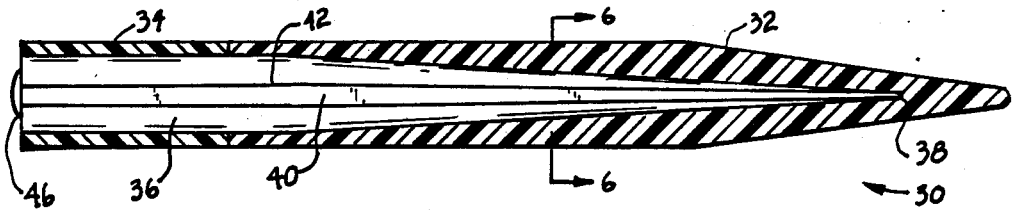
FIG._4.
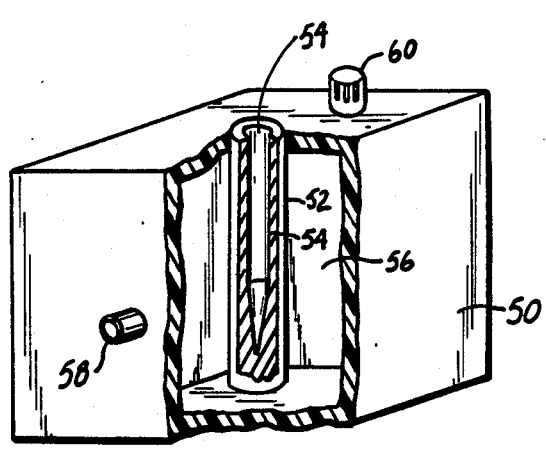
FIG._7.
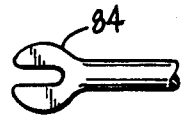
FIG._9.
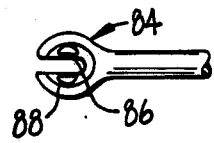
FIG._10.
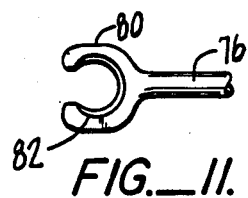
FIG._11.

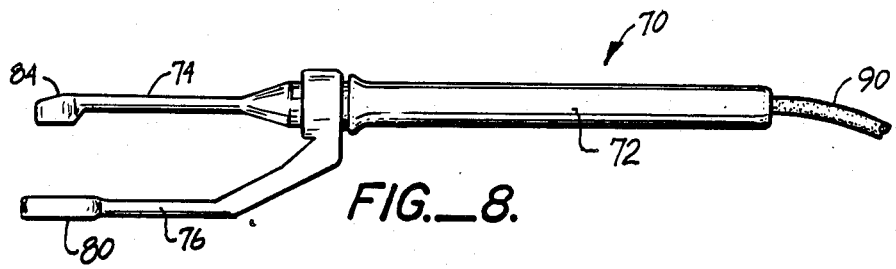
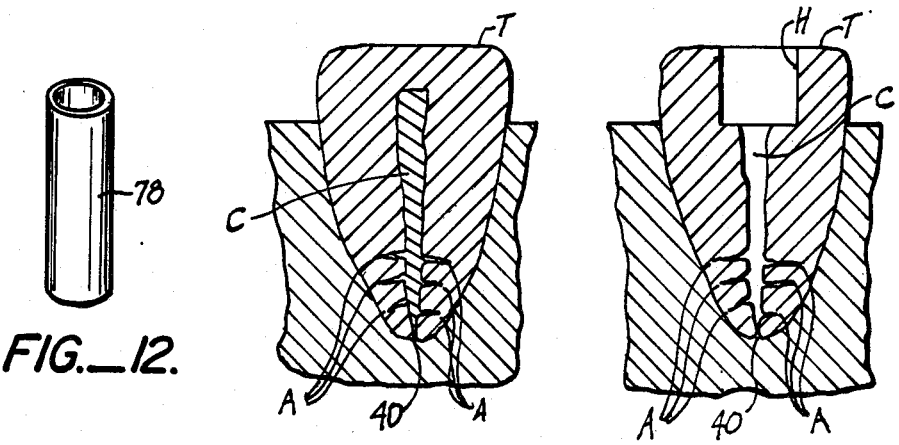
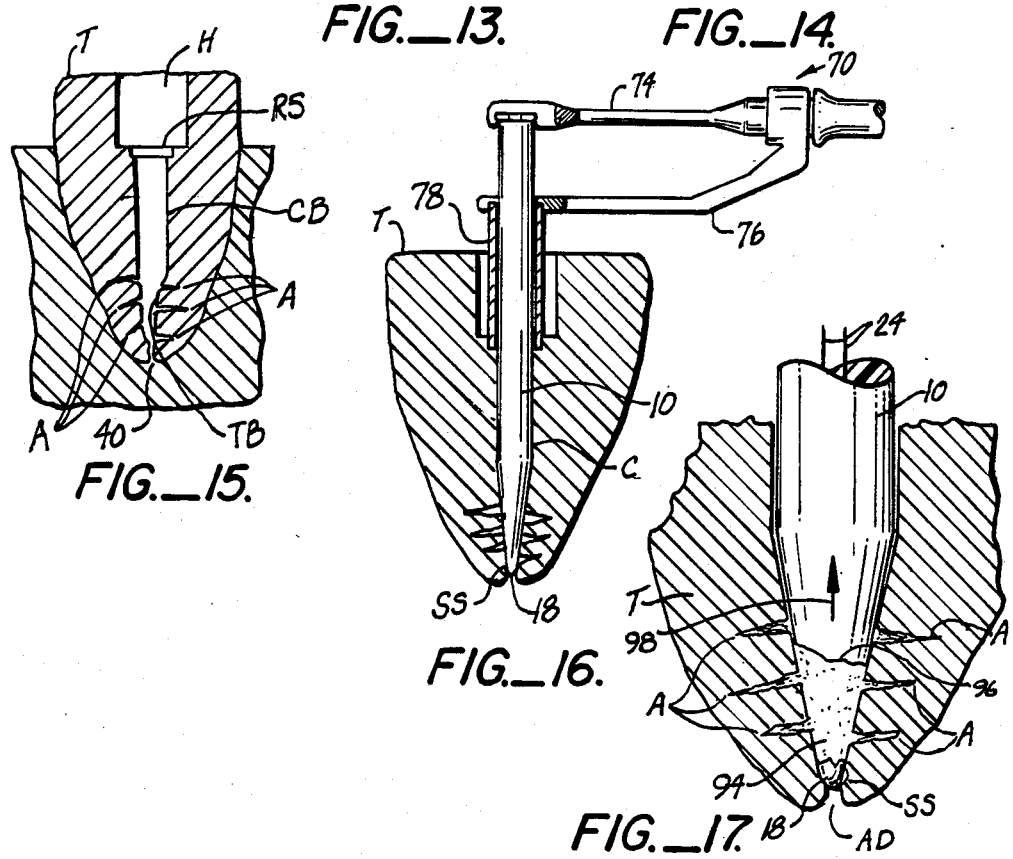

METHOD FOR RAPID OBTURATION OF ROOT CANALS

This is a continuation of Ser. No. 511,373, filed July 5, 1983, now abandoned.

BACKGROUND OF THE INVENTION

1. Field of the Invention

The root system of a tooth can include from one to four major canals extending generally upward from an apical opening at the bottom of the tooth and a plurality of accessory or auxiliary canals opening laterally from the major canals. Conventional root canal therapy comprises cleaning and shaping of the major canals followed by filling the root system in a manner to obturate both the major and accessory canals. In this way, the intrusion of body fluids into the canal system is prevented and possible inflammation is avoided. It is particularly important that the major and accessory canals be completely sealed in order to maintain the integrity of the tooth.

Three techniques for performing root canal therapy are in widespread use today. The first technique, referred to as lateral condensation, relies on inserting a plurality of gutta percha cones to fill the major canal. A first (master) cone is placed to seal the apical opening and a number of accessory cones are used to fill the remainder of the canal. A sharp steel instrument is used to compress the cones and spread the gutta percha in a lateral direction to fill the major and accessory canals. The instrument creates large lateral forces which can fracture the tooth in the absence of extreme care. Moreover, the lowermost cone can be forced through the apical opening and into the surrounding tissue, causing inflammation. In addition, the gutta percha frequently adheres to the compression instrument and, unless the instrument is withdrawn cautiously, the filling will be loosened or displaced as the instrument is removed.

A second technique, referred to as the heated gutta percha technique, relies on the use of a high temperature probe to melt the gutta percha in situ. A cold, lubricated instrument is then used to compact the filling material and to flow such material into the accessory canals. One or more gutta percha cones are emplaced in the major canal and treated in such a manner until the root canal system is filled. Although generally an improvement over the lateral condensation technique, the heated gutta percha technique also suffers from drawbacks. If the heated probe is not removed at precisely the right moment, the melted gutta percha will adhere to the probe and be removed from the tooth. Use of the compacting instrument can apply excessive lateral force and cause tooth fracture or cause the material to pass through the apical opening. Finally, if the heated probe is removed too soon, the gutta percha may not uniformly melt and some of the accessory canals may not be filled.

The third approach to root canal therapy involves the use of compounded pastes and fillers which are packed or injected into the root canal system. Numerous specific techniques have been developed, and the techniques generally suffer from inadequate materials, i.e., the filling materials may be difficult or impossible to remove from the canal, and a tendency to overfill the canal system causing material to flow through the apical opening and into the surrounding tissues. Either of these problems can necessitate oral surgery to correct.

It would thus be desirable to provide a method and system for filling the root canal system which assures that sufficient material is implanted to fully obturate the major canal and all accessory canals, avoids over filling the canal and causing the incursion of material into the surrounding tissues, and avoids the necessity of compacting the filling material by inserting a compaction tool into the major canal and possibly fracturing the tooth by causing excessive lateral forces.

2. Description of the Prior Art

U.S. Pat. Nos. 3,899,830 and 3,949,479 to Malmin describes a system for filling root canals with gutta percha filling points. The filling points may be melted after placement in the tooth by use of an ultrasonic heating device. British Pat. No. 214,497 describes a gutta percha filling point. U.S. Pat. No. 4,357,136 to Herskovitz et al. describes a syringe for injecting heated thermoplastic materials into a prepared root canal.

SUMMARY OF THE INVENTION

The present invention provides a method and system for obturating prepared root canals by heating and softening a thermoplastic filling point in situ within the root canal. The root canal is first prepared according to conventional techniques and the filling point inserted into the major canal. Conveniently, the filling point may be cooled prior to insertion in order to shrink the point and to assure that it fully penetrates the major canal substantially up to the apical opening. The filling points each include an internal heating element which is then activated, causing the thermoplastic material to soften and fill the major and accessory canals. The softened thermoplastic material is caused to flow into the accessory canal by the application of a modest pressure on the top of the filling point itself. The method does not require that any compaction instruments be placed into the canal. Indeed, nothing other than the filling point itself need be inserted into the tooth during the filling operation.

In the preferred embodiment of the invention, the heating element will not extend the entire length of the filling point. The heating element will terminate at a preselected distance from the end of the filling point which lies adjacent the apical opening. In this way, the thermoplastic material near the apical opening softens more slowly and is less able to flow through the apical opening. The remaining length of the filling point softens more rapidly and is able to flow laterally to fill the accessory canals. A second refinement comprises the use of a heating element which heats more rapidly at the end near the apical opening. The material in the upper portions of the filling point thus softens less rapidly and can be compressed downward against the softened material to cause that material to flow into the accessory canals. As the softened zone of material moves upward, the remaining accessory canals are filled.

BRIEF DESCRIPTION OF THE DRAWINGS

FIG. 1 is a sectional view of a first embodiment of the filling point of the present invention.

FIG. 2 is a left end view of the filling point of FIG. 1.

FIG. 3 is a sectional view taken along the line 3—3 of FIG. 1.

FIG. 4 is a sectional view of a second embodiment of the filling point of the present invention.

FIG. 5 is a left end view of the filling point of FIG. 4.

FIG. 6 is a cross-sectional view taken along the line 6—6 of FIG. 4.

FIG. 7 illustrates the cooling device of the present invention.

FIG. 8 illustrates the instrument used for inserting the filling points of the present invention.

FIG. 9 is a top view of the upper fork of the compaction instrument of FIG. 8.

FIG. 10 is a bottom view of the upper fork of the compaction instrument of FIG. 8.

FIG. 11 is a bottom view of the lower fork of the compaction instrument of FIG. 8.

FIG. 12 illustrates the alignment sleeve of the present invention.

FIG. 13 illustrates a tooth prior to root canal therapy.

FIG. 14 illustrates a partially prepared tooth prior to filling by the method of the present invention.

FIG. 15 illustrates a fully prepared tooth prior to filling by the method of the present invention.

FIG. 16 illustrates the manner of insertion of the filling point of the present invention.

FIG. 17 is a detailed view illustrating the manner in which the filling point of the present invention softens and fills the root canal system.

DESCRIPTION OF THE PREFERRED EMBODIMENTS

The method of the present invention relies on the ability to place a thermoplastic filling point into the major canal of a prepared root canal system and to heat the filling point progressively from a point near the apical opening of the canal and progressively upward therefrom. As used herein, upward will refer to the direction away from the apical opening while downward will refer to the direction toward the apical opening. By applying a moderate downward force on the filling point as it is heated, pressure is exerted on the softened lower portions of the filling point, causing them to flow into the accessory canals. As the softened region progresses upward along the filling point, the remaining accessory canals are filled until substantially all have been filled and the root canal system is sealed. To perform this method, a particular system comprising a novel filling point, a novel instrument for compacting the filling point within the tooth, heating and applying pressure on the filling point, and optionally a device for cooling the filling points are provided. Each of these system components will be discussed in order.

The most critical system component is the filling point which is placed into the major root canal and softened to seal both the major canal and the accessory canals. The filling point is fabricated primarily from a bio-compatible, thermoplastic material which will flow when softened or melted by heat. On cooling, the material will harden, typically by cross-linking, to permanently seal the root canal system. Suitable thermoplastic materials include polyethylenes, polypropylenes, nylons, and natural and synthetic rubbers. Particularly preferred is gutta percha which is commonly in use in dentistry and familiar to most practitioners.

Referring now to FIGS. 1-3, the construction of a filling point 10 suitable for the present invention will be described. The filling point 10 includes a first section 12 formed from the thermoplastic material just described and a second section 14 formed from a rigid material which will not deform when heated. The filling point 10 is generally cylindrical having a diameter in the range from about 0.2 to 3.0 millimeters, usually from about 0.7 to 1.0 millimeters, and a length in the range from about 10 to 30 millimeters, usually from about 18 to 25 millimeters. The thermoplastic section 12 terminates in a tapered or conical region 16 having a blunt end 18 at its apex. The blunt end 18 is generally spherically shaped having a diameter of about 0.1 millimeters. The precise dimensions of the filling point 10 are not critical and will depend on the dimensions of the prepared root canal being treated. The dental practitioner will typically maintain a number of filling points having differing dimensions within the ranges set forth above so that a particular filling point having desired dimensions can be selected for any application.

The filling point 10 includes an axial heating element 20. The heating element 20 generally runs from the top end of the filling point 10 to a point within the tapered region 16 of the thermoplastic section 12. As will be discussed in detail hereinafter, the heating element 20 terminates at a point 22 which is spaced inward from the blunt end 18 of the filling point 10. In this way, the blunt end 18 is softened less rapidly than the remaining portions of the thermoplastic section 12. The distance between the terminal point 22 of the heating element and the blunt end 18 is not critical. Generally, the distance will be greater than the radial distance between the heating element 20 and the periphery of the filling point 10. Such a greater distance provides additional thermal mass and resistance between the terminal point 22 of the heating element and the blunt end 18 which slows the softening relative to the remaining thermoplastic portions of the filling point. For a filling point having a diameter of 1.0 millimeter, the distance between the terminal point and the blunt end 18 will exceed 0.5 millimeter, typically being in the range from about 0.5 to 5.0 millimeters, more typically being from about 1.0 to 2.0 millimeters.

The axial heating element 20 will usually be an electrical resistance heating element. Conveniently, the heating element 20 may be a bent wire 24 which forms a circuit between a first connector pad 26 and a second connector pad 28. The connector pads 26 and 28 are conveniently located at the top end of the filling point so that an electrical connection can be made with the compaction instrument, as will be described hereinafter.

It is desirable that the filling point 10 be progressively heated and softened beginning at a location proximate the terminal point 22 and progressing upward toward the top end. Use of the bent wire heating element 24 helps provide such a heating pattern. The electrical resistance in the wire 24 is greatest at the bend (located at terminal point 22) causing the temperature of the heating element 20 to be greatest at that point. The progressive heating effect is enhanced by the tapered shape of region 16 of the filling point 10. As the radial distance between the heating element 20 and the adjacent peripheral region of the filling point 10 increases in the region 16, the thermal mass and resistance increases. Thus, the portions of the filling point 10 closer to the terminal point 22 of the heating element will soften more rapidly than the portions more remote from the terminal point 22.

The heating profile of the heating element 20 may be improved by the use of a conductor having a gradually decreasing cross-sectional area. In this way, a temperature gradient can be provided along a preselected length of the heating element, further assuring that the filling point 10 melts progressively. Such a tapered heating element is illustrated in FIG. 4, as described hereinafter.

The rigid section 14 is provided to facilitate connection of the filling point 10 to the compaction instrument. While the entire length of the filling point 10 could be formed from thermoplastic material, it would be more difficult to grasp the filling point with the compaction tool, particularly after the material had been softened. Moreover, since the rigid section 14 does not deform, pressure can more easily be applied to the thermoplastic section 12 by the compaction instrument.

An alternate embodiment of the filling point is illustrated in FIGS. 4-6. The filling point 30 includes both a first section 32 formed from a thermoplastic material and a second section 34 formed from a rigid material, as described in reference to the first embodiment. The filling point 32 further includes a tapered insert 36 which is axially oriented therein. The insert 36 extends from the top end of the filling point 32 to a point 38 corresponding to the terminal point 22 of the first embodiment. An electrical heating element 40 is formed along the outer surface of the insert 36. The heating element 40 is defined by a ribbon of an electrically conductive material, the ribbon being tapered to a minimum width at the terminal point 38. The other leg of the folded heating element (which is hidden behind the insert 36) is similarly tapered. In this way, the desired heating profile as described above can be obtained. The heating element 40 is connected to connector pads 44 and 46 at the top end of the filling point.

The conical insert 36 is formed from a rigid material which will not deform under the heat of the heating element 40. Normally, pressure will not be applied to the insert 36 during the initial stages of compaction with downward pressure being applied only to the surrounding thermoplastic material 34. After the canal has been substantially filled, however, a very light pressure may be applied downward on the insert 36 to complete the compaction.

The method of the present invention optionally provides for cooling of the filling point prior to insertion into the prepared root canal in order to shrink the point. Depending on the particular thermoplastic material, the filling point should be cooled sufficiently to shrink the point by from about 0.5 to 3%, usually below about $-10°$ C. For the preferred gutta percha filling points, cooling to a temperature in the range from about $-25°$ C. to $-75°$ C. is suitable. The filling points may be cooled by any technique. Because of their low thermal mass, it is desirable that they be cooled immediately prior to insertion.

Conveniently, a portable cooling unit will be provided. The cooling unit can be taken to the patient and the filling point cooled immediately prior to use. The nature of the cooling use is not critical. A suitable unit is illustrated in FIG. 7 and comprises an insulated box 50 having a retaining tube 52 therein. The retaining tube 52 has a well 54 formed therein, and the well 54 is open to the exterior of the box 50 to allow insertion and removal of filling points. The insulated box 50 defines an enclosed cavity 56 surrounding the retaining tube 52. The retaining tube 52 is formed from a heat conductive material, typically aluminum, and introduction of a cooling medium into the cavity 56 will cause chilling of the filling point when placed in the well 54. Conveniently, the cooling device can be connected to a compressed gas, such as carbon dioxide, through a connector 58. The compressed gas may then be released into the insulated box 50 and the expansion of the gas will cause a cooling of the retaining tube 52. Baffles (not shown) will usually be provided within the enclosed cavity 56 to provide some retention of the cooled gases before they exit through a vent 60 on top of the cooling device.

The instrument for compacting the filling point of the present invention into a prepared root canal system is illustrated in FIGS. 8-12. The compaction instrument 70 comprises a handle 72, an upper fork 74 attached at the forward end (i.e., to the left as viewed from FIG. 8) of the handle, and a lower fork 76 slidably received onto the handle 72. An alignment sleeve 78 (FIG. 12) is adapted to fit below the forward end of the lower fork 76. Specifically, a clevis 80 formed in the forward end of the lower fork 76 includes an annular depression 82 which is dimensioned to fit over and hold the upper end of alignment sleeve 12.

A retaining cap 84 is formed at the forward end of the upper fork 74. The lower face of the retaining cap 84, as viewed in FIG. 10, includes a pair of connector pads 86, 88 which are designed to mate with the connector pads 26, 28 or 44, 46 formed on the top end of the filling points 10 or 30, respectively. The compaction instrument 70 is placed on the filling point 10 after the filling point has been placed in the root canal and the alignment sleeve 78 placed over the upper end of the filling point. The compaction tool 70 is placed so that the clevis 80 lies over the upper end of alignment sleeve 78 and the retaining cap 84 lies over the upper end of the filling point 10 (as illustrated in FIG. 16). The orientation of the filling point should be checked to make sure that electrical contact between the contactor pads is achieved.

The compaction instrument 70 should be modified slightly to handle the second embodiment 30 of the filling point. Specifically, the retaining cap 84 should be modified to rest against only the thermoplastic region 34 and not to contact the insert 36. In this way, downward force can be applied to the thermoplastic region without applying force to the insert 36.

The compaction instrument 70 may include an internal (battery) power supply. Alternatively, as illustrated in FIG. 8, the compaction instrument 70 may be connected to an external power supply (not shown) by a power cord 90. The size of the power supply is not critical. Typically, the power supply will be low voltage with a limited current supply to prevent electrical shock. The precise voltage will be selected to provide the appropriate heating of the filling points and will depend on the resistance characteristics of the heating elements.

Referring now to FIGS. 13-17, the method of the present invention will be described in detail. FIG. 13 illustrates a tooth T prior to any preparation. Preparation of the root canal C is conventional except where noted. First, the tooth is drilled to provide access to the main canal of the root canal system. This results in a drilled hole H (FIG. 14) formed in the upper surface of the tooth T. The pulp is then removed from the main canal, typically using a broach according to conventional techniques. The canal is further prepared by drilling to a predetermined depth to form a generally cylindrical bore CB, as illustrated in FIG. 15. The diameter of the cylindrical bore CB is the minimum necessary to clean the inner surface of the root canal. Unlike prior art methods of root canal treatment, there is no tendency to further widen the bore CB to facilitate the insertion of compaction tools. The remaining length of the main canal C is then bored using a reamer to form a tapered bore TB having its apex terminating just above the apical opening AO of the root canal. Typically, the cylindrical bore CB will extend over the upper two-thirds of the main canal, while the tapered bore TB extends over the lower one-third. It is in the lower one-third of the canal that most of the accessory canals A are located.

Prior to inserting the filling point, a stop seat SS (best illustrated in FIG. 17) and rest seat RS (FIG. 15) are formed at opposite ends of the canal C. The stop seat SS allows the full insertion of the filling point, as will be described hereinafter. The rest seat RS receives the lower end of the alignment sleeve 78 and helps assure the proper alignment of the compaction tool during the compaction of the filling point.

The tooth T is now ready to receive the filling point 10 or 30. Based on the earlier measurement of the root canal depth and the known diameter of the cylindrical bore CB, an appropriately-sized filling point is selected. When the point is to be cooled, a point which is slightly larger than the canal is chosen. The filling point is then fully inserted into the root canal using forceps. Prior to cooling, the blunt end 18 of the point should not quite reach the stop seat SS. The practitioner can usually feel such contact. If it occurs, a slightly larger point can be selected. The filling point is then marked to indicate the expected insertional depth and removed and inspected. The insertional depth is checked against the measured depth of the canal (taking the cooling effect into account), and if the two agree, the filling point can be used.

At this point, the filling point should be cooled, typically to a temperature in the range from $-25°$ C. to $-75°$ C. for gutta percha filling points. The cooling device described earlier can be used, or any other technique employed. To help achieve quick cooling, the well 54 of the cooling device 50 may be partially filled with alcohol to increase the heat transfer rate. Such cooling shrinks the filling point facilitating its full insertion into the prepared canal and improving the sealing of both the apical opening and accessory canals.

Prior to final insertion of the filling point into the canal C, the canal is coated with a conventional cement. The filling point 10 is then fully inserted into the canal C and the alignment sleeve 78 placed over the upper end of the filling point. The compaction instrument 70 is then attached to the filling point 10 and alignment sleeve 78, as described hereinabove and illustrated in FIG. 16.

After all components of the system are in place, the power is turned on and the practitioner applies a gentle downward force on the handle 72. The filling point 10 will begin to soften in an area 94 (FIG. 17) located above the blunt end 18 of the filling point 10. For the reasons described above, a transition line 96 between the softened and non-softened regions in the filling point will develop and move upward in the direction of arrow 98. The practitioner continues to apply power and a gentle downward force on the filling point until the canal is substantially filled. This will be apparent because the compaction of the filling point will cease. Once the compaction ceases, the thermoplastic material will have filled into the accessory canals A as illustrated in FIG. 17. The power may then be stopped and the compaction instrument 70 removed. The rigid section 14 of the filling point 10 can then be removed, typically by cutting or twisting, and the remaining thermoplastic material compacted. The exposed upper surface of the tooth is then filled in the normal manner.

Although the foregoing invention has been described in some detail by way of illustration and example for purposes of clarity and understanding, it will be obvious that certain changes and modifications may be practiced within the scope of the appended claims.

What is claimed is:

1. An improved filling point for sealing a prepared root canal cavity, said filling point having a length in the range from 10 to 30 mm and including an axial electrically resistive heating element which is fixedly imbedded within the filling point, whereby after sealing said root canal cavity with said filling point, said resistive heating element remains fixedly part of said filling point.

2. An improved filling point as in claim 1, wherein the heating element terminates at a point spaced inward from one end thereof.

3. An improved filling point as in claim 2, wherein the filling point includes a cylindrical portion and is conically tapered at said one end.

4. A filling point as in claim 1, wherein the heating element includes electrical connectors formed at the other end of the elongate body.

5. A filling point for sealing a prepared root canal cavity, said filling point comprising:
    an elongated body having a length in the range from 10 to 30 mm and which is tapered at one end and formed from a thermoplastic material; and
    an electrically resistive heating element defined by a wire which is disposed axially within the elongate body and which runs from the other end of the body to a point spaced inward from the tapered end and which is bent at said point so that it runs back to said other end, said element including means for attaching both ends of the wire to a current source whereby after sealing said root canal cavity with said filling point, said resistive heating element remains fixedly part of said filling point.

6. A filling point as in claim 5, wherein the heating element is a conductor running from the other end of the body to the termination point, being bent backward at the termination point, and running back to the other end.

7. A filling point as in claim 5, wherein the electrically resistive heating element has a reduced cross-sectional area near the termination point.

8. A filling point as in claim 5, wherein a portion of the elongate body at the other end is formed from a deformation-resistant material.

9. A filling point as in claim 5, wherein the elongate body includes a core formed from a deformation-resistant material.

10. A method for sealing a prepared root canal system including the major canal having an apical opening and a plurality of accessory canals, said method employing an elongate filling point tapered at one end and comprised of thermoplastic material and having an integral heating element, said method comprising:
    placing the filling point in the major canal with the tapered end of the filling point adjacent the apical opening of the major canal;
    heating the filling point by means of the heating element beginning generally at the tapered end and moving toward the other end so that the filling point softens progressively from the tapered end to the other end; and applying a downward force on the filling point while heating so that as each portion of the filling point softens, that portion is caused to flow laterally into the accessory canals by force which is transmitted downward through the unsoftened portion of the filling point.

11. A method as in claim 10, further comprising the step of cooling the filling point prior to placing the filling point in the major canal to effect shrinkage.

12. A method as in claim 10, wherein the apex of the tapered end is heated less rapidly than other portions of the filling point so that the thermoplastic material is less likely to flow through the apical opening of the major canal.

13. A filling point for sealing a prepared root canal cavity, said filling point comprising:

an elongate body which is formed from a thermoplastic material at one end and from a deformation-resistant material at the other end, said one end also being tapered; and a heating element which is disposed axially within the elongate body and which terminates at a point spaced inward from the tapered end.

14. A filling point for sealing a prepared root canal cavity, said filling point including an axial electrically resistive heating element extending from one end of the filling point to an internal point spaced inward from the other end of the filling point, and connector pads at the one end for electrically connecting the heating element to a compaction instrument capable of supplying electric current to the connector pads.

15. A filling point for sealing a prepared root canal cavity, said filling point comprising:

an elongated body which is tapered at one end and formed from a thermoplastic material, where a portion of the body at the other end is formed from a deformation resistant material; and an electrically resistive heating element which is disposed axially with the elongate body and terminates at a point spaced inward from the tapered end and includes means for attaching to a current source at the other end.

* * * * *